(12) United States Patent
Falkenstein et al.

(10) Patent No.: US 7,909,819 B2
(45) Date of Patent: Mar. 22, 2011

(54) MONOPOLAR ELECTROSURGICAL RETURN ELECTRODE

(75) Inventors: Zoran Falkenstein, Rancho Santa Margarita, CA (US); John R. Brustad, Dana Point, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1162 days.

(21) Appl. No.: 11/469,738

(22) Filed: Sep. 1, 2006

(65) Prior Publication Data

US 2008/0058792 A1 Mar. 6, 2008

(51) Int. Cl.
*A61B 18/16* (2006.01)
(52) U.S. Cl. .................... 606/32; 606/35; 600/372
(58) Field of Classification Search ............ 606/32–35
See application file for complete search history.

(56) References Cited

U.S. PATENT DOCUMENTS

| | | | |
|---|---|---|---|
| 3,768,482 A | 10/1973 | Shaw | |
| 4,117,846 A * | 10/1978 | Williams | 606/32 |
| 4,269,189 A * | 5/1981 | Abraham | 606/32 |
| 5,308,311 A | 5/1994 | Eggers et al. | |
| 5,366,443 A | 11/1994 | Eggers et al. | |
| 5,433,732 A | 7/1995 | Hirschberg et al. | |
| 5,480,399 A * | 1/1996 | Hebborn | 606/35 |
| 5,624,452 A | 4/1997 | Yates | |
| 5,697,281 A | 12/1997 | Eggers et al. | |
| 5,697,882 A | 12/1997 | Eggers et al. | |
| 5,697,909 A | 12/1997 | Eggers et al. | |
| 5,716,366 A | 2/1998 | Yates | |
| 5,766,153 A | 6/1998 | Eggers et al. | |
| 5,871,469 A | 2/1999 | Eggers et al. | |
| 5,929,744 A | 7/1999 | Duggal et al. | |
| 6,053,910 A * | 4/2000 | Fleenor | 606/32 |
| 6,083,221 A | 7/2000 | Fleenor et al. | |
| 6,132,426 A | 10/2000 | Kroll | |
| 6,142,992 A | 11/2000 | Cheng et al. | |
| 6,159,194 A | 12/2000 | Eggers et al. | |
| 6,224,592 B1 | 5/2001 | Eggers et al. | |
| 6,238,391 B1 | 5/2001 | Olsen et al. | |
| 6,309,387 B1 | 10/2001 | Eggers et al. | |
| 6,312,408 B1 | 11/2001 | Eggers et al. | |
| 6,413,255 B1 | 7/2002 | Stern | |
| 6,454,764 B1 * | 9/2002 | Fleenor et al. | 606/32 |
| 6,544,258 B2 | 4/2003 | Fleenor et al. | |
| 6,582,424 B2 | 6/2003 | Fleenor et al. | |
| 6,602,252 B2 | 8/2003 | Mollenauer | |
| 6,623,454 B1 | 9/2003 | Eggers et al. | |
| 6,632,220 B1 | 10/2003 | Eggers et al. | |
| 6,666,859 B1 | 12/2003 | Fleenor et al. | |
| 6,743,223 B1 * | 6/2004 | Lang | 606/32 |
| 6,770,071 B2 | 8/2004 | Woloszko et al. | |
| 6,770,072 B1 | 8/2004 | Truckai et al. | |
| 6,821,273 B2 | 11/2004 | Mollenauer | |

(Continued)

*Primary Examiner* — Linda C Dvorak
*Assistant Examiner* — Amanda Scott
(74) *Attorney, Agent, or Firm* — Patrick Y. Ikehara; John F. Heal

(57) ABSTRACT

A monopolar electrosurgical return electrode to prevent unwanted thermal effects in monopolar electrosurgery, accomplished in one aspect by volumetric incorporation of temperature-resistive material of positive nature into a flexible and adhesive return electrode pad is provided. The incorporation of positive temperature coefficient resistance with low resistance at room temperature will increase the local electrical resistance of the pad with an increase of the local return electrode temperature corresponding to a switching of the resistance from low to high value which in turn will lead to a reduction of the local current density. The switching temperature of the positive temperature coefficient return electrode is low enough to prevent significant thermal heating of the patient's tissue.

10 Claims, 5 Drawing Sheets

U.S. PATENT DOCUMENTS

| | | |
|---|---|---|
| 6,837,888 B2 | 1/2005 | Ciarrocca et al. |
| 6,843,789 B2 | 1/2005 | Goble |
| 6,893,435 B2 | 5/2005 | Goble |
| 6,905,497 B2 | 6/2005 | Truckai et al. |
| 6,926,716 B2 | 8/2005 | Baker et al. |
| 6,929,644 B2 | 8/2005 | Truckai et al. |
| 6,960,204 B2 | 11/2005 | Eggers et al. |
| 7,288,091 B2 * | 10/2007 | Nesbitt ........................ 606/45 |
| 2002/0165531 A1 | 11/2002 | Goble |
| 2003/0040741 A1 | 2/2003 | Fleenor et al. |
| 2003/0078573 A1 | 4/2003 | Truckai et al. |
| 2003/0078577 A1 | 4/2003 | Truckai et al. |
| 2003/0078578 A1 | 4/2003 | Truckai et al. |
| 2003/0139741 A1 | 7/2003 | Goble et al. |
| 2003/0171748 A1 | 9/2003 | Truckai et al. |
| 2003/0195513 A1 | 10/2003 | Truckai et al. |
| 2003/0199870 A1 * | 10/2003 | Truckai et al. .................. 606/51 |
| 2003/0208201 A1 | 11/2003 | Iida et al. |
| 2003/0212444 A1 | 11/2003 | Truckai et al. |
| 2003/0220637 A1 | 11/2003 | Truckai et al. |
| 2004/0078035 A1 | 4/2004 | Kanehira et al. |
| 2004/0087937 A1 | 5/2004 | Eggers et al. |
| 2004/0116979 A1 | 6/2004 | Truckai et al. |
| 2004/0199161 A1 | 10/2004 | Truckai et al. |
| 2004/0215184 A1 | 10/2004 | Eggers et al. |
| 2004/0215185 A1 | 10/2004 | Truckai et al. |
| 2005/0096651 A1 | 5/2005 | Truckai et al. |
| 2005/0131402 A1 | 6/2005 | Ciarrocca et al. |
| 2005/0159745 A1 | 7/2005 | Truckai et al. |
| 2005/0171535 A1 | 8/2005 | Truckai et al. |
| 2005/0187543 A1 | 8/2005 | Underwood et al. |
| 2005/0192568 A1 | 9/2005 | Truckai et al. |
| 2005/0203507 A1 | 9/2005 | Truckai et al. |
| 2005/0234439 A1 | 10/2005 | Underwood |
| 2005/0261678 A1 | 11/2005 | Truckai et al. |
| 2005/0288665 A1 | 12/2005 | Woloszko |
| 2006/0000823 A1 | 1/2006 | Truckai et al. |
| 2006/0224150 A1 * | 10/2006 | Arts et al. ....................... 606/32 |

* cited by examiner

MONOPOLAR ELECTROSURGICAL RETURN ELECTRODE

BACKGROUND

The present invention relates to the field of monopolar electrosurgery, and in particular to a monopolar electrosurgical return electrode.

Monopolar electrosurgical cutting and/or coagulation systems provide electrical current from an electrosurgical unit (ESU) to the active electrode, from where it is flows through the tissue to be cut and/or coagulated. While the supplied electrical current subsequently disperses through the patient body, it is ultimately collected within the return electrode to be returned to the ESU.

In this cycle flow, the current density at the interface between active electrode and tissue is moderate to high to perform the desired cutting and/or coagulation action, whereas the current density through the patient's body, as well as at the return electrode are low to prevent electrical burns. Even though the total current though the active electrode is the same as at the return electrode, the vast difference in current densities is due to largely different areas of the active electrode and the return electrode. The significant difference in current densities can change when either the return electrode is not connected properly to the patient, or when one or more sections of the return electrode accidentally separate from the patient's body. As such, unregulated or unchecked current density at the return electrode can cause unwanted thermal affects. It has also been found that a current density in excess 5 of 100 milliamperes per square centimeter would heat the body tissue beyond the threshold of necrosis.

SUMMARY

The present invention generally provides a monopolar current-limiting electrosurgical return electrode.

In one aspect, a monopolar electrosurgical return electrode comprises a flexible pad doped with a positive temperature coefficient thermistor material and a conductor attached to the flexible pad. The flexible pad is adapted to receive an adhesive conductive gel and arranged to increase in resistance to at least more than 100 Ohms at at least 45 degrees Celsius.

In one aspect, a monopolar electrosurgical return electrode comprises a flexible pad having a polymer base with a surface area of less than 100 square centimeters, an electrically resistive substrate embedded in the polymer base having a surface area of less than 100 square centimeters, and a positive temperature coefficient thermistor material, polycrystalline ceramic with barium titanate with silica. The return electrode also comprises a metallic foil attached to the polymer base of the flexible pad.

In one aspect, a monopolar electrosurgical return electrode comprises a flexible pad adapted to contact a patient's skin without manipulating an instrument, means for increasing electrical resistance to at least more than 100 Ohms at at least 45 degrees Celsius, and a connector attached to the flexible pad.

Many of the attendant features of the present invention will be more readily appreciated as the same becomes better understood by reference to the following detailed description and considered in connection with the accompanying drawings in which like reference symbols designate like parts throughout.

DETAILED DESCRIPTION

Figure 1:
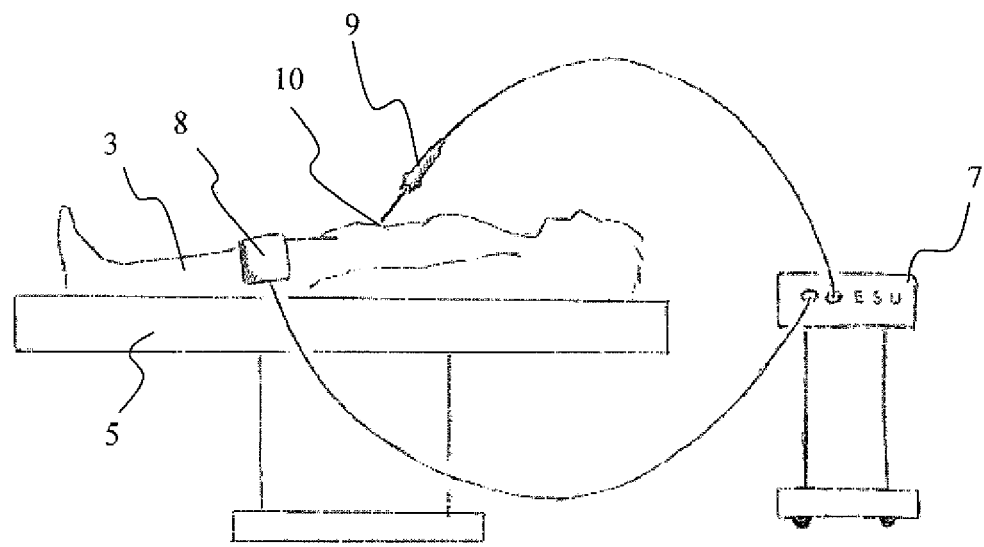
FIG. 1 is a schematic diagram of the electrical circuit for monopolar electrosurgery.

In FIG. 1, monopolar electrosurgery on a patient 3 resting on an electrically isolated surgical table 5 is shown being performed by supplying alternating radiofrequency (RF) electrical current from an electrosurgical unit (ESU) 7 to a hand-held or laparoscopic electrosurgical instrument with an active electrode 9. Depending on the electrosurgical process (cutting, coagulation, desiccation, fulguration, etc.), the electrical power is supplied from the ESU 7 in sinusoidal, pulsed, or mixed modes; in the frequency range of 100 kHz to 1 MHz; and voltages ranging from few tens of volts to a few kilovolts. If the active electrode 9 is in close proximity to, or in light contact with the patient's tissue 10, electrical current flows (at high to medium current density) to the tissue to perform the electrosurgical effect. Taking the path of least resistance through the patient's body, the supplied electrical current flows (at very low current density) towards a return electrode 8, where it gathers to be returned to the ESU 7. The return electrode 8 is configured to limit current. As such, the return electrode 8 prevents an uncontrolled rise of current density even locally, and as a result does not allow a significant rise in tissue temperature that may lead to electrical burning. In one aspect, the return electrode 8 is configured with a temperature-dependant resistance. As such, any increase in the (local) current density beyond a defined and predetermined limit will lead to heating of the return electrode material, causing an increase in the (local) temperature and thus temperature-dependant resistance of the return electrode 8, which in turn reduces and ultimately ceases the (local) electrical current, opposed to further heating the tissue 10.

Figure 2A:
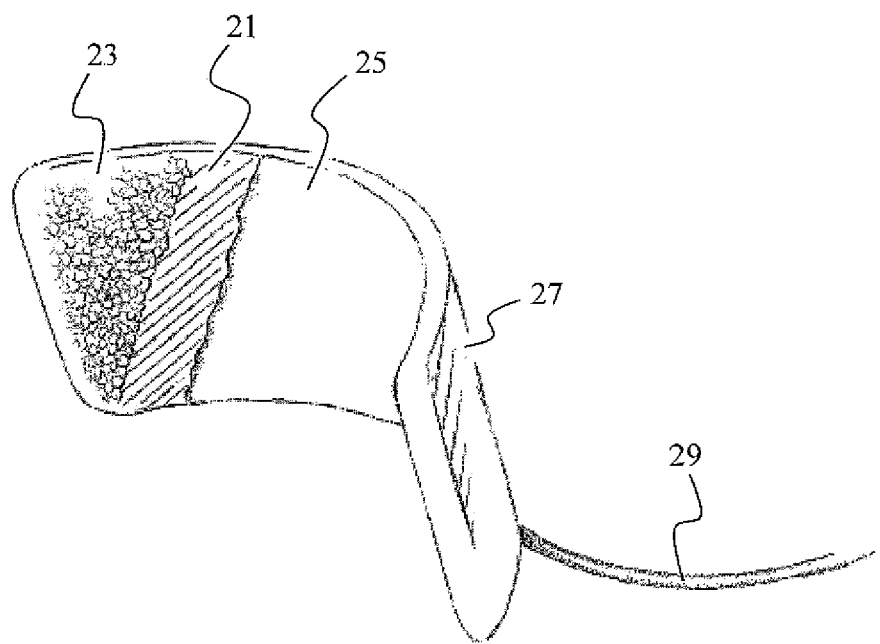
FIG. 2A-C shows a cross-section of the flexible PTC-doped return electrode pads in accordance with various aspects of the present invention.

In FIG. 2A, a return electrode 8 provides an effective electrical contact area. The flexible pad 21 doped with a positive temperature coefficient (PTC) thermistor material 23, finely dispersed and distributed volumetrically within the soft and flexible electrode base material. The PTC material can be made of a polycrystalline ceramic material that is normally highly resistive, but is made semi-conductive by the addition of dopants. They include, but not limited to, compositions of barium, lead and strontium titanates with additives such as yttrium, manganese, tantalum and silica. The flexible pad is silicone, rubber, plastic or other types of flexible material able to be doped with the PTC thermistor material. The flexible pad is compact being about 100 cubic square inches. The soft conductive electrode is secured to the patient by an electrically conductive adhesive gel 25 disposed over the entire active area of the return electrode. Thus, instead of relying on the patient resting on the return electrode, the disposable return electrode can be applied to numerous effective positions on the body. As such, the surgeon is provided much more flexibility in moving the patient into different positions during surgery and also reduces the return path of the electricity through the body by placing the return electrode on specific effective locations. The opposing side of the pad is applied to a metallic foil 27, which attaches to a wire lead 29 to connect to the ESU 11.

The return electrode in one aspect has a resistance that is low at room temperature and increases, switching of resistance from low to high, with an increase of the local return electrode temperature resulting in a reduction in the local current density. The switching of resistance occurs at a predetermined switching temperature or temperature range that is sufficiently low to prevent unwanted thermal affects to the patient tissue. The relationship of resistance to temperature and the predetermined switching temperature for the return electrodes, described herein, are provided more below in reference to FIGS. 3-6. In one aspect, a feedback or control circuit is added into or provided with the ESU to monitor the resistance between return electrode and patient's tissue. If the resistance fails out of a specific predetermined range, the ESU or control circuit activates an audio or visual alarm, disengages or limits the supplied RF energy or deactivates.

Figure 2B:
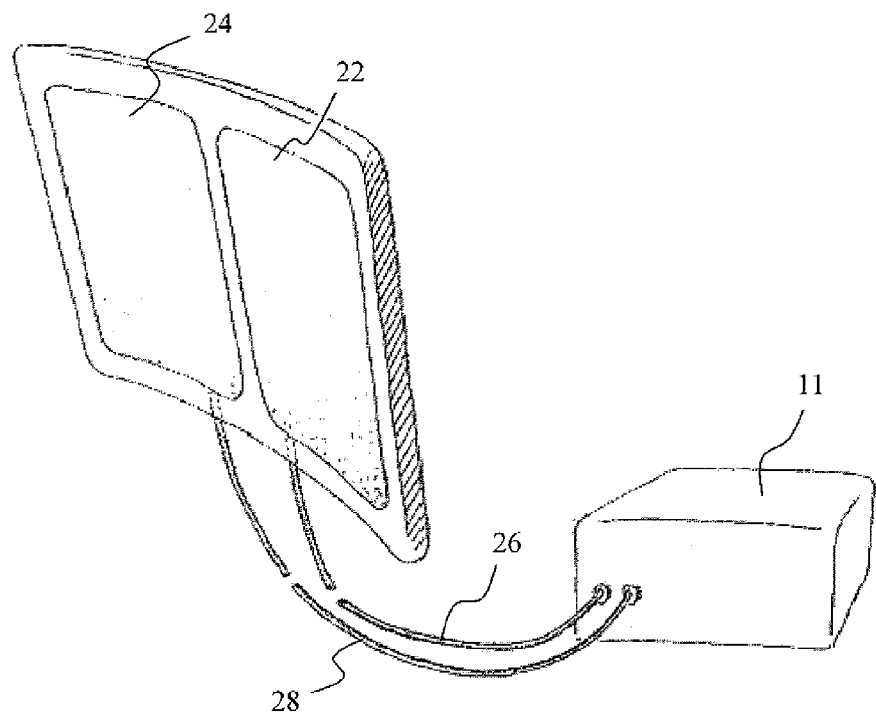

In FIG. 2B, the PTC-based return electrode is provided as "split" electrode, and is connected to the ESU 11. In particular, the active electrode area of the PTC-doped flexible and adhesive return electrode is split into two electrically isolated segments 22, 24. Each electrode segment collects the electrical return current and returns it to the ESU 11 along two separate paths 26, 28. This local separation of the return current allows the ESU 11 to monitor the intensity of each return current. If the two currents differ from more than an acceptable range, the ESU, for example via a control circuit, activates an alarm, disengages the power and/or deactivates itself. Possible causes for a significant difference in return current from the two segments 22, 24 can be one segment of the return electrode not properly being connected, as may happen, as the electrode pad is de-laminating, or placing the electrode in a non-suited fashion onto the patient. The latter is the case when the geometric location of the return electrode allows the return current to prefer one segment from the electrode pad.

In one aspect, both the resistance between the entire return electrode and the patient, as well as any difference in partial electrical current through the electrode segments 22, 24 are being monitored by the ESU 11 before and during engaging power to ensure that both the entire return electrode, as well as each section of the electrode is properly connected to the patient. Use of a "split" electrode however can increase surgery cost and may require a compatible ESU to recognize and/or handle the separate return currents. The "split" return electrode with PTC material would also cause an increase of the resistance by one or both electrode segments due to heating of the return electrode.

Figure 2C:
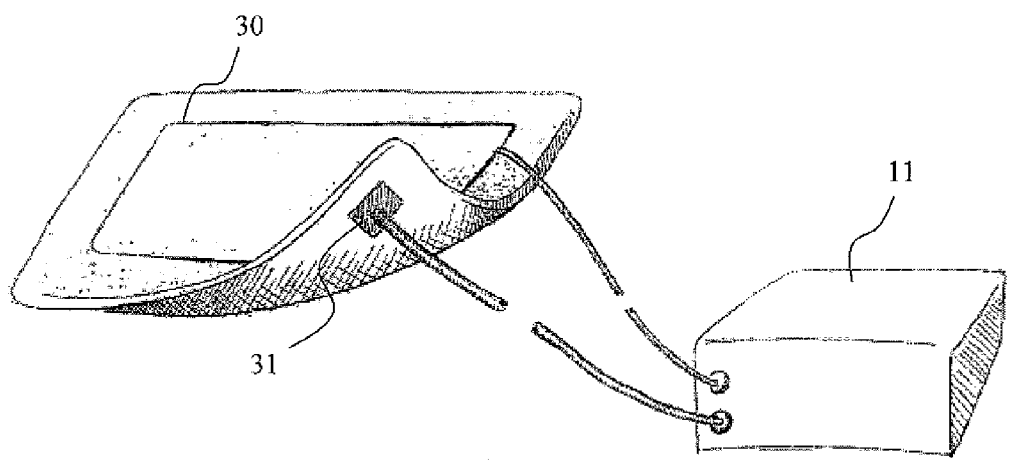

In FIG. 2C, the active electrode area of the PTC-doped flexible and adhesive return electrode is provided with two connectors 30, 31 extending therefrom or attached therewith. The first connector 30 outlines a portion of the active electrode area and the second connector 31 is coupled to the opposing side of the active electrode area. In one aspect, the first connector 31 is a metallic lining arranged in a substantially rectangular pattern on the active electrode area, although the material, size, dimension and pattern may vary. Also, although the material, size, dimension and pattern may vary, the second connector, in one aspect, is a metallic foil strip extending from the return electrode. By connecting the second lower metallic foil of the return electrode, as well as a metallic lining on the opposing side of the electrode to the ESU 11, the resistance across a "single-patch" PTC-electrode could be monitored by the ESU (which is equipped to monitor "split" electrodes). Likewise, the ESU and/or the control circuitry provided with or incorporated into the ESU would decrease excessive current in monopolar electrosurgery by providing an alarm, disengaging or limiting the supplied RF energy or deactivating the ESU, due to a temperature increase of the return electrode.

Figure 3:
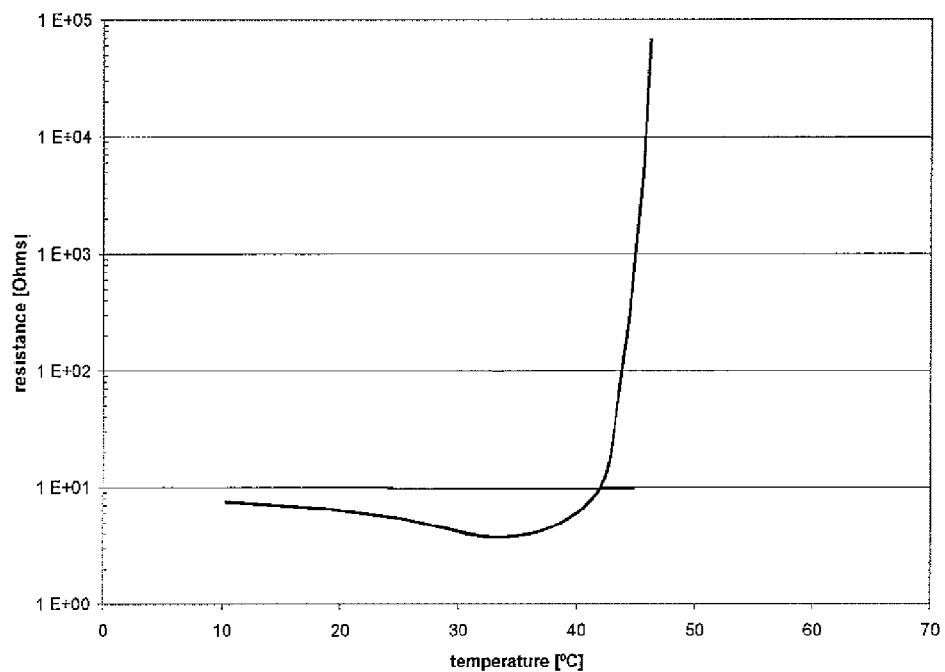
FIG. 3 is a graphical representation of the ohmic resistance of positive temperature coefficient doped return electrode as function of temperature in accordance with various aspects of the present invention.

FIG. 3 graphically exemplifies the resistance-temperature characteristics of the PTC material embedded into the base electrode material. While the material exhibits low resistance of only a few Ohms with a very small negative temperature coefficient from low to ambient temperatures (about 30° C.), it shows a rising, positive temperature coefficient of resistance (about 35 to 40° C.) when the temperature approaches the Curie switch or transition temperature, and a very large increase in resistance at the Curie temperature (about 45° C.). The increase in resistance at this point can be as much as several orders of magnitude within a temperature span of only a few degrees. As such, the PTC-doped return electrode can be viewed as an electrical switch changing from a conductor to a non-conductor.

Figure 4A:
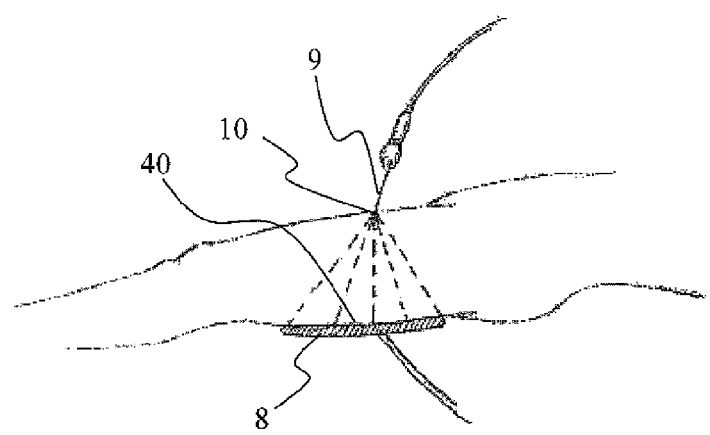
FIGS. 4a through 4c illustrate exemplary current densities at the active and return electrodes.
Figure 4B:
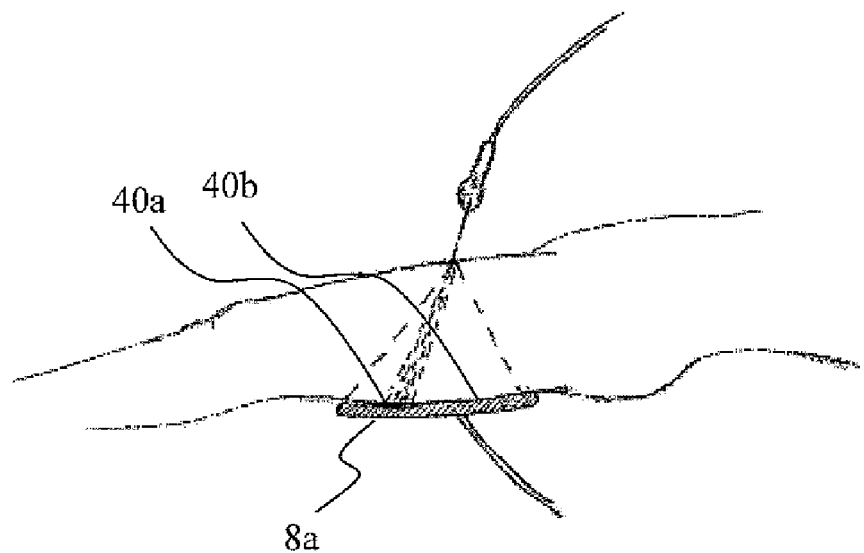
Figure 4C:
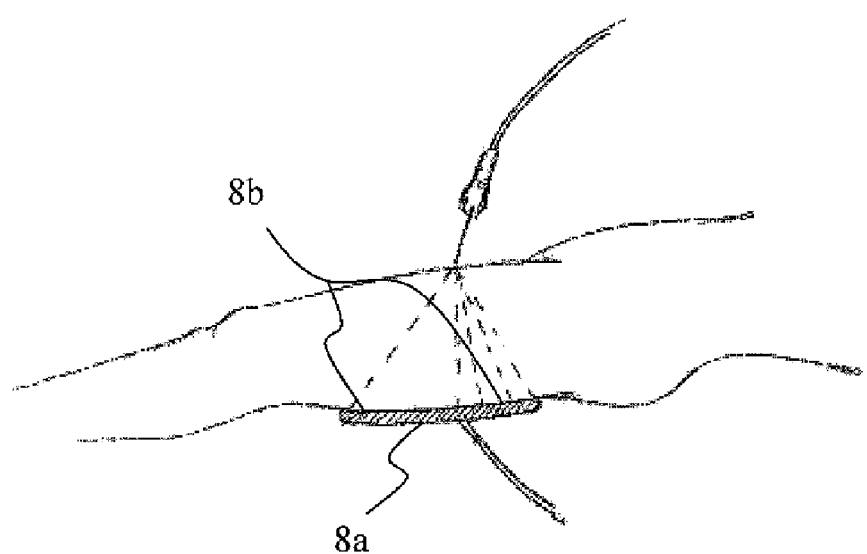

The effect of the temperature-dependant change in resistance is depicted in FIGS. 4A through 4C. As shown in FIG. 4A, at "normal" conditions, the electrical power will be supplied by the ESU 11 at high or moderate current density to the tissue 10 by the active electrode 9, dispersed through the body at low current density and returns through the tissue 40 contacting the PTC-doped return electrode 8 at very low current density. This allows for no nominal heating of both the tissue and the return electrode 8, which maintains the material to be electrically conductive. If however, as shown in FIG. 4b, the current density at the tissue location 40a is locally higher than at the remainder of the tissue 40b, it consequently will lead to unequal heating of both the tissue 40a,b and the locally connecting return electrode 8a. This, in turn, will increase the local resistance of the electrode segment, up to complete switching, which will locally cease the current. As shown in FIG. 4c, the current flows through neighboring electrode areas 8b until the temperature has dropped again below switching temperature, in which case the local area 8a will "participate" in returning the current again. Since the area of the (locally) switched electrode area 8a is usually very small in comparison the "bulk" electrode area 8b, the temperature increase and the overall resistance of the bulk electrode will remain unchanged.

Figure 5:
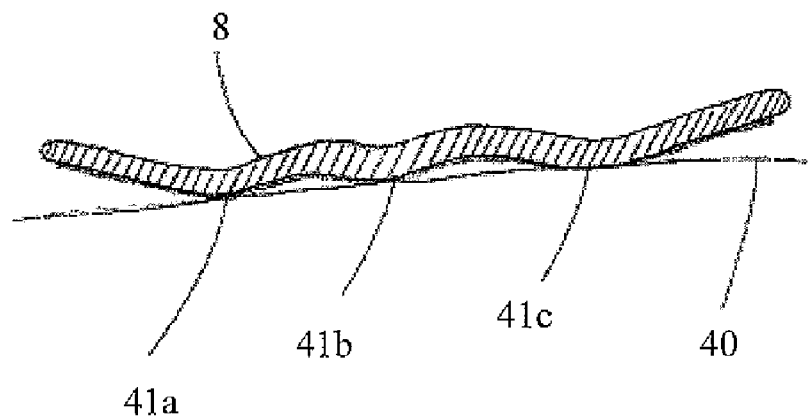
FIG. 5 shows a return electrode that is only partly connected to the patient, or which is de-laminating from the patient.

This is different if a large fraction, of a continuously increasing fraction of the PTC return electrode switches due to a continuous increase in temperature, as can be in the case with a poorly connected, or progressively de-laminating return electrode. This case is shown in FIG. 5, where the contact area(s) 41a-c of the electrode 8 with the tissue 40 is too small for proper operation, or reduces continuously, causing the current density to increase continuously. This in turn increases the temperature and resistance of the electrode up to and including switching temperature, which at about 45° C. is low enough not to burn the tissue.

If the overall electrode has switched to a nonconductor, the overall resistance has increased, causing a complete interruption of the current. In this case the surgeon will not be able to provide current from the activated electrode through the tissue. Instead, the patient will be on the same electrical potential as the active electrode, with the full voltage drop across the switched return electrode. As the return electrode gradually cools, and becomes conductive again, the electricity will dissipate to the properly reattached return electrode.

A particular application of the invention might be with the utilization of the invention in combination with the current feedback mechanism provided by the ESU. For example, when operating the return electrode on an ESU providing resistance metering of the tissue (also called "AutoCut" or "AutoCoag" modes), the increase in overall resistance of the return (patch) electrode due to a "fault" can be used to stop the power supply of the ESU.

Figure 6:
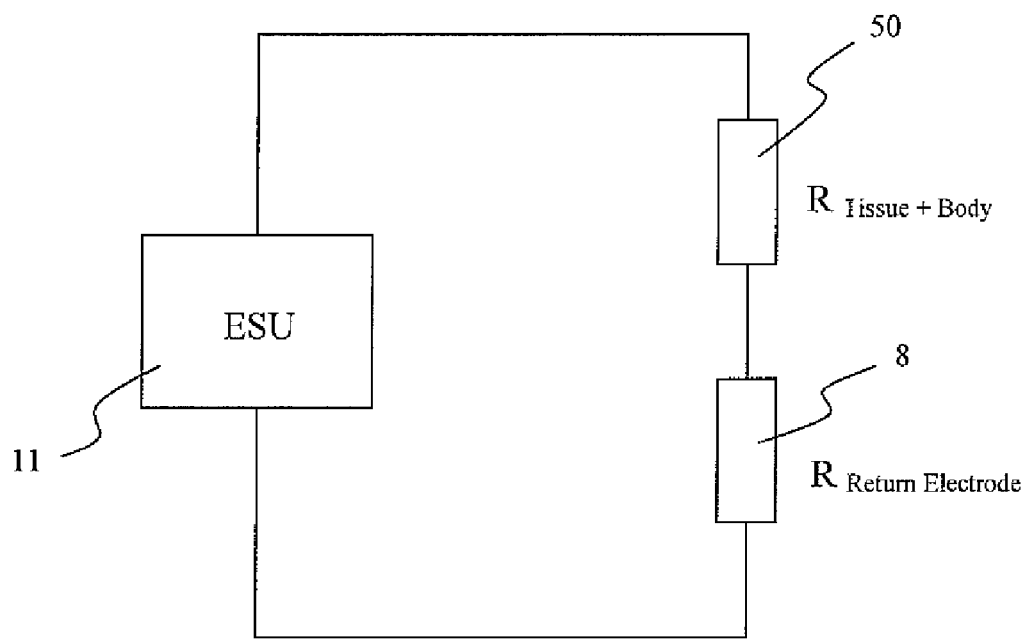
FIG. 6 shows an electrical diagram for monopolar electrosurgery in accordance with various aspects of the present invention.

FIG. 6 shows the electrical schematic diagram for monopolar electrosurgery, where the ESU 11 is connected to the treated tissue and patient's body 50 through the active electrode (not shown), as well as the return electrode 8. Under "normal" condition, the effective resistance of the (untreated) tissue and patient are in the range of about one hundred to less than one thousand Ohms, and the un-switched PTC-return electrode adds only a few ten Ohms to the circuit. The ESU will detect the end of cutting and/or coagulation due to the resistive change in the tissue. At the same time, the ESU will also detect a strong resistive increase in the return electrode (which increases to several kilo Ohms and higher) under "faulty" conditions, and subsequently terminate the supply of further power.

The following provides existing feedback loops in monopolar electrosurgery, where the strong increase in electrical resistance with switching of the bulk return electrode could be detected by the feedback mechanism usually used for "split" electrodes. In these systems, the ESU monitors the resistance between the two "split" electrode segments (before and during supplying power), and typically sounds an alarm if the resistance is higher than usually few ten Ohms, and even to the power if the resistance is larger than about one hundred Ohms.

Possible causes for an increase in current density beyond a nominal value could be a local concentration of the return current from the patient site, an improperly connected return electrode, or possibly even a de-lamination of the electrode from the patient's tissue. In the first case, the increase in the local return pad temperature beyond switching temperature will cause the local resistance to increase dramatically, which will drive the return current to flow through neighboring electrode areas until the temperature of the switched electrode section has dropped again below the switching temperature of the PTC-doped electrode. At this point, the local area will again participate in returning the current from the patient to the properly connected return electrode.

In the second case, an increased return current density will also cause the resistance of the electrode to increase. However, since the contact area between the return electrode and the body tissue might be too small to ensure a (locally) safe return current density which occurs in the third case with a de-laminating electrode pad progressive heating of the entire return electrode leads to switching of the entire electrode still connected to the patient. As the electrode material heats to the switching temperature of the PTC-material, the strong increase in resistance will prevent any further current being driven through the electrical circuit.

While in the first case the local increase of electrode resistance will "divert" the current to neighboring electrode areas, allowing the affected electrode area and tissue to cool, the fully switched electrode pad in the latter case will electrically interrupt the electrical circuit to protect the patient. In this case, the entire supplied voltage will be lying across the return electrode, and with the exception of a minimal leakage current too small to heat the tissue, no current will be flowing through the circuit (and the patient).

Accordingly, the present invention provides a current-limiting monopolar electrosurgical return electrode. Although this invention has been described in certain specific embodiments, many additional modifications and variations would be apparent to those skilled in the art. It is therefore to be understood that this invention may be practiced otherwise than specifically described, including various changes in the size, shape and materials, without departing from the scope and spirit of the present invention. Thus, embodiments of the present invention should be considered in all respects as illustrative and not restrictive, the scope of the present invention to be determined by the appended claims and their equivalents rather than the foregoing description.

The invention claimed is:

1. A monopolar electrosurgical return electrode comprising:
    a flexible pad doped with a positive temperature coefficient thermistor material, the flexible pad adapted to receive an adhesive conductive gel and arranged to increase in resistance to at least more than 100 Ohms at least 45 degrees Celsius, the pad having a surface area of less than 100 square centimeters;
    wherein the thermistor material reduces current density to 100 mA per square centimeter or less at 45 degrees Celsius or higher; and
    a conductor attached to the flexible pad.

2. The electrode of claim 1 wherein the thermistor material comprises polycrystalline ceramic with dopants, the dopants being one of barium, lead and strontium titanates with additives, the additives being one of yttrium, manganese, tantalum and silica.

3. The electrode of claim 1 wherein the pad has a polymer base having a surface area of less than 100 square centimeters, and an electrically resistive substrate embedded in the polymer base having a surface area of less than 100 square centimeters.

4. The electrode of claim 1 wherein the electrode is disposable.

5. The electrode of claim 1 further comprising an adhesive conductive gel arranged on a substantial surface area of the flexible pad to adhere the pad to a patient's skin.

6. The electrode of claim 1 wherein the conductor is coupled to an electrosurgical unit with a feedback circuit to monitor one of interface resistance between tissue and the return electrode and current driven through the tissue to the return electrode.

7. In combination with the electrode of claim 1, further comprising an active electrode configured to communicate electrical current to the return electrode, the active electrode having a surface area substantially smaller than a surface area of the return electrode.

8. The electrode of claim 7 wherein the active electrode and the return electrode are coupled to an electrosurgical unit with a feedback circuit to monitor one of resistance between the electrodes and difference in electrical currents through the electrodes.

9. The electrode of claim 1 wherein the flexible pad is adapted to contact a patient's skin without manipulating an instrument.

10. The electrode of claim 1 wherein the thermistor material comprises polycrystalline ceramic with barium titanates with silica.

* * * * *